US011504551B2

(12) United States Patent
Wu et al.

(10) Patent No.: US 11,504,551 B2
(45) Date of Patent: Nov. 22, 2022

(54) SYSTEM FOR ADJUSTING RADIATION TARGET SITES DYNAMICALLY ACCORDING TO MOVING STATES OF TARGET OBJECT AND FOR CREATING LOOKUP TABLE OF THE MOVING STATES

(71) Applicants: Jian-Kuen Wu, Taipei (TW); Yu-Jen Wang, New Taipei (TW)

(72) Inventors: Jian-Kuen Wu, Taipei (TW); Yu-Jen Wang, New Taipei (TW)

( * ) Notice: Subject to any disclaimer, the term of this patent is extended or adjusted under 35 U.S.C. 154(b) by 252 days.

(21) Appl. No.: 15/931,549

(22) Filed: May 13, 2020

(65) Prior Publication Data

US 2021/0275832 A1 Sep. 9, 2021

(30) Foreign Application Priority Data

Mar. 4, 2020 (TW) .................................. 109107078

(51) Int. Cl.
*A61N 5/10* (2006.01)

(52) U.S. Cl.
CPC ........... *A61N 5/1068* (2013.01); *A61N 5/107* (2013.01); *A61N 5/1075* (2013.01); *A61N 2005/1076* (2013.01)

(58) Field of Classification Search
CPC .. A61N 5/1064; A61N 5/1065; A61N 5/1067; A61N 5/1068; A61N 5/107
See application file for complete search history.

(56) References Cited

U.S. PATENT DOCUMENTS

| 9,351,782 | B2 | 5/2016 | Vaughn | |
|---|---|---|---|---|
| 2008/0021300 | A1* | 1/2008 | Allison | ................ A61N 5/1031 378/65 |
| 2013/0070898 | A1* | 3/2013 | Stahl | .................... A61N 5/1045 378/65 |
| 2014/0275704 | A1* | 9/2014 | Zhang | .................. A61N 5/1067 600/1 |

FOREIGN PATENT DOCUMENTS

| CN | 203943681 U | 11/2014 |
|---|---|---|
| CN | 109891050 A | 6/2019 |
| WO | 2019096986 A1 | 5/2019 |

\* cited by examiner

*Primary Examiner* — Carrie R Dorna
(74) *Attorney, Agent, or Firm* — CIPO IP Group

(57) ABSTRACT

A system for adjusting radiation target sites dynamically according to the moving states of a target object and for creating a lookup table of the moving states includes a detection chip, a radiation generation device, and a lookup table. The detection chip can be fixed on the target object to detect the current moving state of the target object. The detection chip or the radiation generation device, both configured for wireless signal transmission to each other, can activate or deactivate the radiation emitters of the radiation generation device individually according to the current moving state of the target object and the contents of the lookup table. As the system uses wireless transmission, and the lookup table has recorded the working state of each radiation emitter in each moving state of the target object, radiotherapy can be performed without a large number of tubes or sensors.

12 Claims, 5 Drawing Sheets

SYSTEM FOR ADJUSTING RADIATION TARGET SITES DYNAMICALLY ACCORDING TO MOVING STATES OF TARGET OBJECT AND FOR CREATING LOOKUP TABLE OF THE MOVING STATES

CROSS-REFERENCE TO RELATED PATENT APPLICATION

This non-provisional application claims priority to and the benefit of, under 35 U.S.C. § 119(a), Taiwan Patent Application No. 109107078, filed in Taiwan on Mar. 4, 2020. The entire content of the above identified application is incorporated herein by reference.

FIELD

The present disclosure relates to a system for use in radiation therapy, and more particularly, relates to a system in which a detection chip can detect the current moving state of a target object and is wirelessly connected to a radiation generation device in order to activate or deactivate a plurality of radiation emitters individually.

BACKGROUND

The incidence rate of cancer in humans has increased significantly along with human life expectancy, which has become a major medical issue faced by humankind in the twenty-first century. According to the 2019 statistics issued by the Ministry of Health and Welfare of Taiwan, for example, cancer has topped the ten leading causes of death in Taiwan for seven years in a row, which is alarming. In light of such, the treatment for cancer has advanced rapidly in the last few decades, resulting in treatment methods such as surgical resection or excision, radiation therapy (or radiotherapy for short), chemical therapy (or chemotherapy for short), and targeted therapy.

Generally speaking, surgical resection or excision has always been the most direct method of cancer treatment. However, cutting out cancer-affected body parts completely (e.g., in the case of a patient with breast cancer on only one side of the body, removing the breast and lymph nodes on the affected side in their entirety) tends to cause severe physical suffering and a great sense of loss. The current trend of cancer treatment, therefore, typically entails removing only the tumor itself and the affected lymph nodes, plus radiotherapy or other therapies in order to achieve the same therapeutic effect as complete removal of the cancer-affected body part. Radiotherapy cures a cancer by means of focused high-energy radiation (e.g., X-rays, electron beams, protons, or heavy particles) that destroys the genetic material, or more specifically DNA, of cancer/tumor cells to inhibit regeneration of and kill those cells and thereby reduce the tumor.

Nowadays, a lot of radiotherapies are available for use, including stereotactic ablative radiotherapy (SABR), three-dimensional conformal radiotherapy (3DCRT), intensity-modulated radiation therapy (IMRT), and volumetric-modulated are radiotherapy (VMAT), among others. A physician would choose an appropriate treatment method based on the type of the cancer to be treated, the size and severity of the tumor, and the patient's physical conditions. SABR, for example, is an ablative radiation therapy whose precision depends on a high-standard positioning technique. SABR requires high-end radiation technology and equipment, and uses a computer to compute an optimal radiotherapy plan. As SABR allows high-dose radiation per treatment, the required number of treatments is relatively small. Moreover, a cancer patient receiving SABR is free from the risks, wound pain, and potential infections associated with surgical operations and is therefore allowed to maintain his or her life quality.

Radiation can destroy not only cancer cells but also the normal tissues surrounding the cancer cells. It is hence imperative to aim a radiotherapy instrument precisely at the tumor to be treated and thereby protect the normal tissues and organs around the tumor. Practically, however, a tumor in the chest or abdomen tends to move away from the radiation target site as the patient breathes. To avoid problems attributable to such movement, the patient may have to receive respiratory gating, active breathing coordination (ABC), deep inspiration breath hold (DIBH) radiotherapy, surface image guided radiation therapy (SIGRT), or other procedures in order to reduce radiation coverage of the normal tissues around the tumor and thereby alleviate the side effects of radiotherapy.

The foregoing procedures require dozens of tubes and sensors to be provided around a patient so that the patient's breathing state can be accurately detected to enable timely activation of the radiotherapy instrument during treatment (e.g., to activate the radiotherapy instrument only when the patient temporarily stops breathing). The large number of tubes and sensors are nevertheless bound to interfere with certain propagation paths of radiation and thus cause problems in use. The issue to be addressed by the present disclosure is to reduce the tubes and sensors required and thereby solve the aforesaid problems effectively.

SUMMARY

In one aspect, the present disclosure is directed to a system for adjusting radiation target sites according to moving states of a target object. The system includes a detection chip, a radiation generation device and a lookup table. The detection chip is configured to be fixed on the target object, and to detect and acquire a current moving state of the target object. The radiation generation device has a plurality of radiation emitters arranged to correspond to different positions on the target object respectively. The radiation emitters are configured to emit radiation when activated. The radiation generation device is configured to transmit signals to and receive signals from the detection chip wirelessly. The lookup table is stored in the detection chip or the radiation generation device. At least one of the detection chip and the radiation generation device is configured to respectively activate or deactivate each of the radiation emitters dynamically according to the current moving state of the target object and contents of the lookup table, so that the radiation emitter emits or does not emit radiation. Accordingly, a patient receiving radiotherapy only has to have the detection chip attached to his or her body, and the radiation generation device will be able to carry out the radiotherapy precisely on the target body portion without having to use a large number of tubes or sensors around the patient's body, greatly enhancing convenience of use.

Another aspect of the present disclosure is directed to a system for creating a lookup table of moving states of a target object. The system includes a dummy, a quantitative detector, a radiation generation device, a detection chip, and an information processing device. The dummy is provided with an elevating platform configured to back-and-forth displace at least a portion of the dummy so as to simulate human body movements. The quantitative detector is located in the dummy. The radiation generation device has a plurality of radiation emitters arranged to correspond to different positions on the dummy respectively. The radiation emitters are configured to emit radiation to be received by the quantitative detector. The detection chip is configured to be mounted on the dummy. The detection chip includes a direction sensing module and a control module. The direction sensing module is configured to detect and acquire at least one moving state of the dummy, and generate a sensing message corresponding to the moving state. The control module is electrically connected to the direction sensing module and configured to receive the sensing message, determine movement information corresponding to the sensing message, and generate a movement message corresponding to the movement information. The information processing device is electrically connected to the quantitative detector and the detection chip respectively. The information processing device is configured to receive the movement message from the detection chip, receive radiation data and information of positions on the dummy that correspond to the radiation data from the quantitative detector, and record at least one of the movement message, the radiation data, and the information of positions on the dummy that correspond to the radiation data in the lookup table stored in the information processing device, so that the lookup table includes the activation/deactivation state of each radiation emitter in each recorded moving state of the dummy.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION

Figure 1:
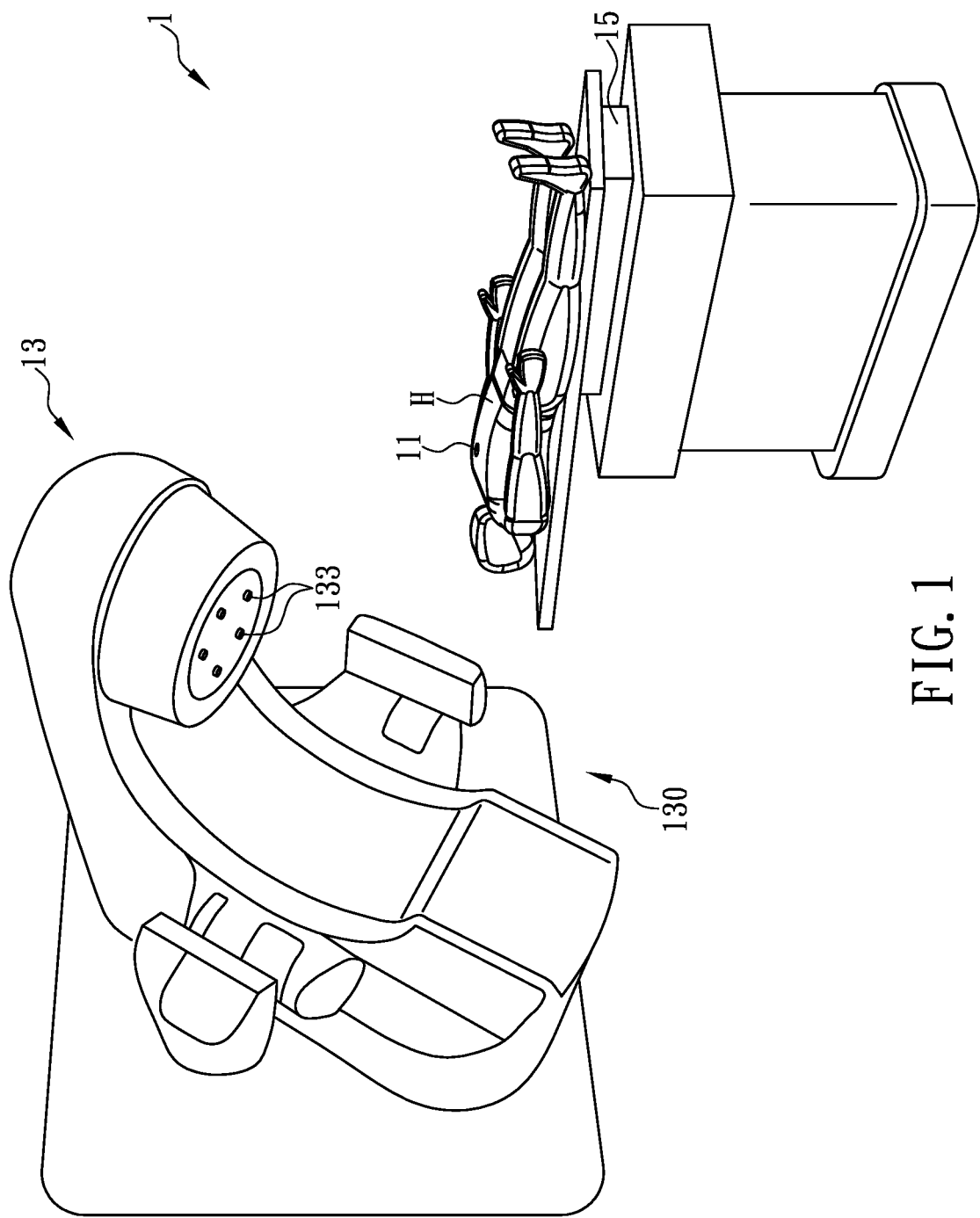
FIG. 1 is a schematic view of a system for adjusting radiation target sites dynamically that is in a state of use according to certain embodiments of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, parts or the like, which are for distinguishing one component/part from another one only, and are not intended to, nor should be construed to impose any substantive limitations on the components, parts or the like.

Figure 2:
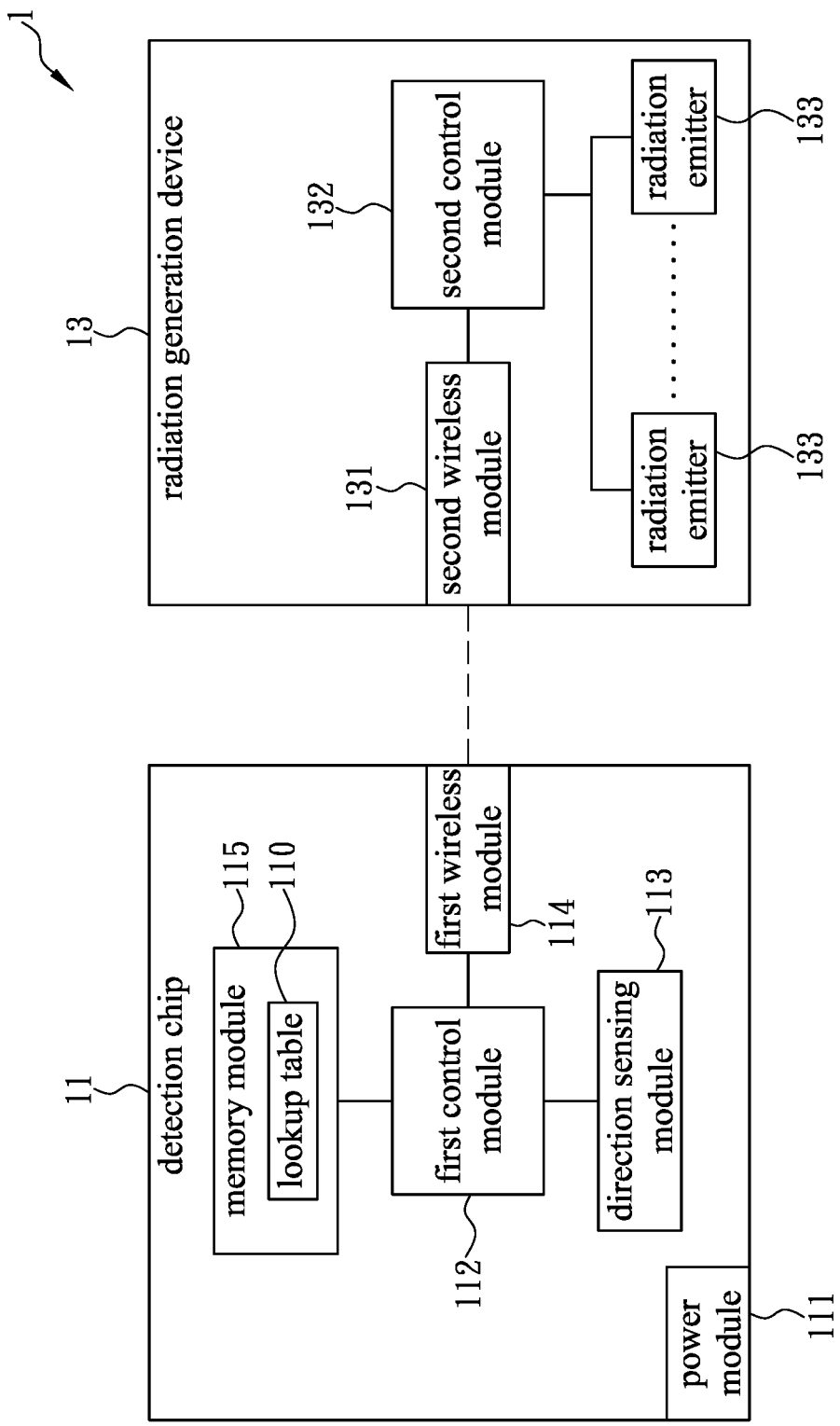
FIG. 2 is a first schematic diagram of the system for adjusting radiation target sites dynamically according to certain embodiments of the present disclosure.

The present disclosure provides a system for adjusting radiation target sites dynamically according to the moving states of a target object and for creating a lookup table of the moving states. Referring to FIG. 1 and FIG. 2, in certain embodiments, the system 1 includes a detection chip 11, a lookup table 110, and a radiation generation device 13. The detection chip 11 is configured to be fixed on a target object H such as a human body or a dummy. For example, the detection chip 1 is fixed on a person's chest when intended to detect the back-and-forth movements of the chest during respiration. The detection chip 11 may also be fixed on a person's abdomen. However, the present disclosure is not limited thereto.

With continued reference to FIG. 1 and FIG. 2, the detection chip 11 stores the lookup table 110 and at least includes a power module 111, a first control module 112, a direction sensing module 113, and a first wireless module 114. The power module 111 (e.g., a battery) supplies the electricity needed to maintain normal operation of all the other modules in the detection chip 11, and is configured to transmit electricity to each module directly or indirectly. It is noted that for the sake of simplicity only, FIG. 2 omits the power transmission lines through which the power module 111 transmits electricity to the other modules. Nevertheless, in view of the description of the present disclosure, a person skilled in the art would be able to understand the techniques related to the electricity supply from the power module 111. In addition, while FIG. 2 shows the power module 111 as located in the detection chip 11, the power module 111 may instead be an independent device and be provided outside the detection chip 11 to ensure safe use of electricity while a patient is being treated with the system 1 and to minimize interference from the power module 111. The connection between the detection chip 11 and the power module 111 may vary as needed, provided that the power module 111 can supply electricity to and sustain normal operation of the detection chip 11, and any such connection shall fall within the scope of the connection relationship between the detection chip 11 and the power module 111 according to the present disclosure.

As shown in FIG. 2, the first control module 112 is electrically connected to the direction sensing module 113 and the first wireless module 114 respectively to transmit signal(s) between the first control module 112 and the direction sensing module 113 and between the first control module 112 and the first wireless module 114. Further, the first control module 112 is configured to read the information in the lookup table 110. In certain embodiments, the lookup table 110 is stored in a memory module 115 of the detection chip 11. In certain embodiments, the memory module 115 may be integrated to the first control module 112 as a single unit, such that the lookup table 110 is located in the first control module 112. Moreover, while FIG. 2 shows the memory module 115 as located in the detection chip 11, the memory module 115 may instead be an external device (e.g., a Universal Serial Bus flash drive) connected to the detection chip 11. In other words, the memory module 115 may be a built-in device or external device.

With continued reference to FIG. 1 and FIG. 2, the direction sensing module 113 is configured to detect and thereby acquire the moving state of the target object H (or more specifically of the detection chip 11), generate a sensing message corresponding to the moving state of the target object H, and send the sensing message to the first control module 112. The direction sensing module 113 may be a gyroscope, an accelerometer (G-sensor), or a combination of the above. In certain embodiments, the direction sensing module 113 can be a combination of a three-axis gyroscope and a three-axis accelerometer, detect six degrees of freedom (6DoF), and thereby acquire the current displacement state of the detection chip 11 (e.g., the moving state in each of the forward, rearward, leftward, rightward, upward, and downward directions). Nevertheless, the direction sensing module 113 may be configured to detect more or fewer degrees of freedom according to practical needs. As long as a direction sensing module can satisfy respective user requirements (e.g., 3DoF, 6DoF, or 9DoF), and detect the current displacement state of the detection chip 11, it falls within the scope of the direction sensing module 113 of the present disclosure.

In certain embodiments, with continued reference to FIG. 1 and FIG. 2, the first wireless module 114 is configured to connect with and transmit signals to and from, under a communication protocol such as Bluetooth (version 4.0 or above), Zigbee, 5G, Ultra-wideband (UWB), or WiFi, etc., a second wireless module 131 in the radiation generation device 13. To avoid or reduce radio-frequency (RF) interference from a nearby instrument (e.g., an accelerator) during use, the first wireless module 114 may be adopted with Bluetooth 4.0 or other communication protocols and equipment that are not subject to accelerator interference. In response to receiving the sensing message corresponding to the moving state of the target object H, the first control module 112 reads the information in the lookup table 110, and converts, based to the lookup table 110, the sensing message into a control message corresponding to the sensing message. The technical means for creating the contents of, or information in, the lookup table 110 will be further described infra. The first control module 112 sends the control message to the radiation generation device 13 through the first wireless module 114 and the second wireless module 131 in order for the radiation generation device 13 to execute procedures corresponding to the control message.

It is noted that the transmission between the first wireless module 114 and the second wireless module 131 may be in a direct mode or indirect mode. In other words, the first wireless module 114 may send the control message directly to the second wireless module 131; or, to a terminal device (e.g., a smartphone or tablet computer) that relays the control message to the second wireless module 131 (i.e., indirect transmission of the control message). In the latter case, the terminal device may add the desired operation command(s), parameter(s), or information into the control message in order for the radiation generation device 13 to execute the procedure(s) corresponding to the control message added with desired operation command(s), parameter(s), or information. In certain embodiments, the first wireless module 114 may send the control message to the second wireless module 131 as well as the terminal device at the same time, and the terminal device can generate an additional control message corresponding to the control message received, and send the additional control message to the second wireless module 131, so that the radiation generation device 13 can execute the procedure(s) corresponding to each of the control message and the additional control message.

Referring again to FIG. 1 and FIG. 2 (while FIG. 2 shows only the essential components of the radiation generation device 13, in view of the description of the present disclosure, a person skilled in the art would still be able to comprehend and apply the radiation generation device 13), the radiation generation device 13 is provided with a plurality of radiation emitters 133. The target object H is placed (or lies) on a carrying table 15. The carrying table 15 is configured to move the target object H into a receiving space 130 of the radiation generation device 13, such that the radiation emitters 133 correspond to different positions on the target object H respectively, and direct the radiation emitted by the radiation emitters 133 to the target object H. It is noted that the receiving space 130 may vary in configuration, and as long as a receiving space of the radiation generation device 13 allows the radiation emitted by the radiation emitters 133 to reach the target object H, such a receiving space falls within the receiving space 130 defined in the present disclosure.

As shown in FIG. 2, in certain embodiments, the radiation generation device 13 includes a second control module 132 configured to receive the control message from the second wireless module 131 and, according to the contents of the control message, instruct each individual radiation emitter 133 to emit or not to emit radiation, for example, activating or deactivating each radiation emitter 133 individually. For example, referring to FIG. 3, which shows a tumor S in a human chest H1, while the human chest H1 is in an exhaling state, the tumor S is at a relatively low position (e.g., below the solid-line boundary of the human chest H1 in FIG. 3), and while the human chest H1 is in an inhaling state, at a relatively high position (e.g., below the dashed-line boundary of the human chest H1 in FIG. 3). The radiation emitter 133A will be activated to emit high-dose radiation to the tumor S when the human chest H1 is in an exhaling state, with the radiation emitter 133B deactivated to avoid irradiating the normal tissues and organs adjacent to the tumor S. By the same token, the radiation emitter 133B will be activated to emit high-dose radiation to the tumor S when the human chest H1 is in an inhaling state, with the radiation emitter 133A deactivated to avoid irradiating the normal tissues and organs adjacent to the tumor S.

Figure 4:
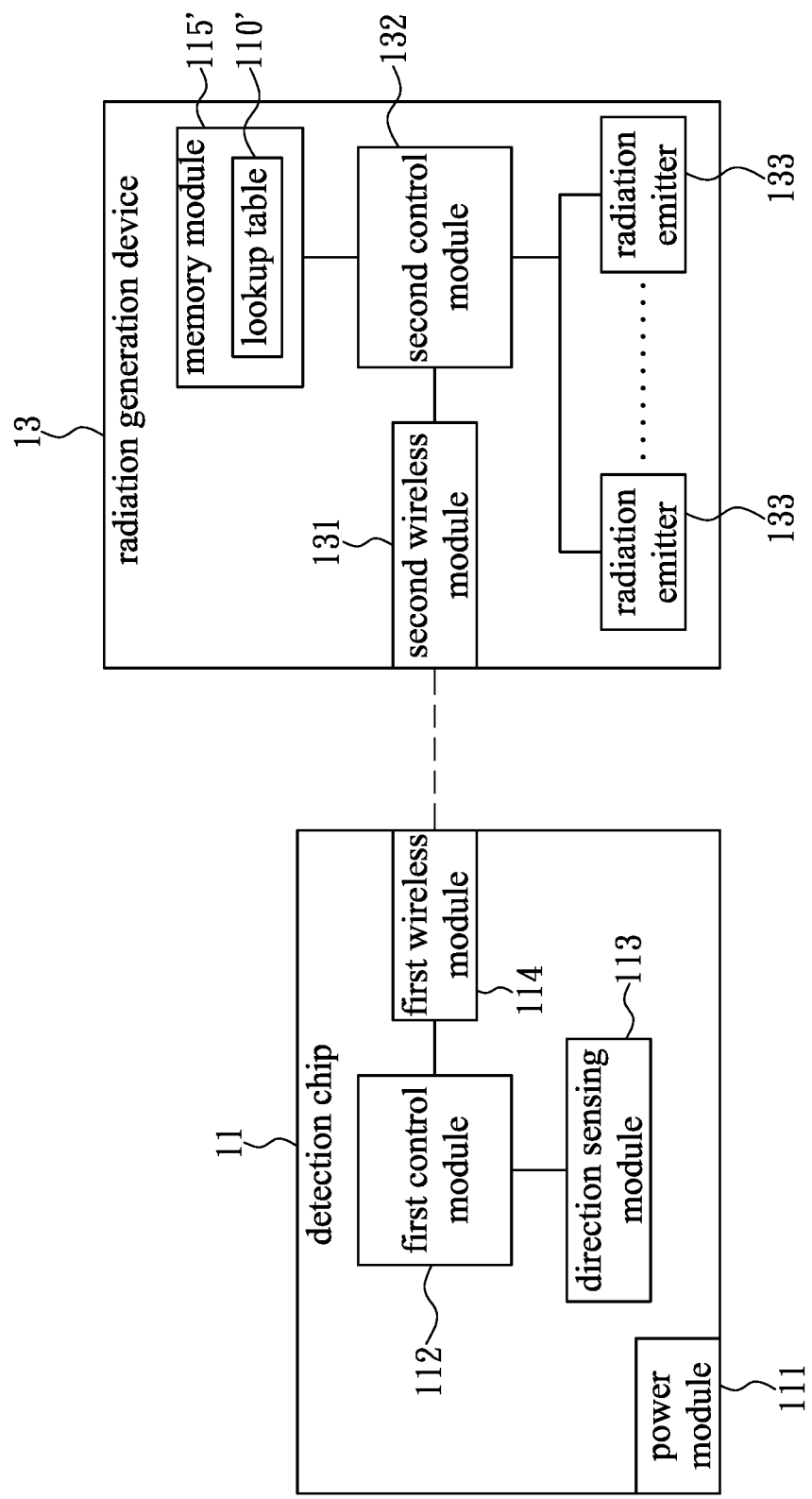
FIG. 4 is a second schematic diagram of the system for adjusting radiation target sites dynamically according to certain embodiments of the present disclosure.

Apart from storing the lookup table in the detection chip 11, in certain embodiments, the lookup table is stored in the radiation generation device 13. Referring to FIG. 4 (in which only elements different from their counterparts in FIG. 2 are indicated by different reference numerals to facilitate description), the radiation generation device 13 is further provided with a memory module 115' for storing a lookup table 110'. The first control module 112 receives the sensing message, and in response to receiving the sensing message, sends out the sensing message through the first wireless module 114. In response to the radiation generation device 13 receiving the sensing message, the second control module 132 reads the lookup table 110', and converts the sensing message into a control message corresponding to the sensing message according to the lookup table 110', so as to respectively activate or deactivate each of the radiation emitters 133 dynamically for each of the radiation emitters 133 to emit or not emit radiation. In certain embodiments, the first control module 112 and the direction sensing module 113 may be integrated as a single unit to accelerate transmission of the sensing message through the first wireless module 114 to the radiation generation device 13.

Figure 5:
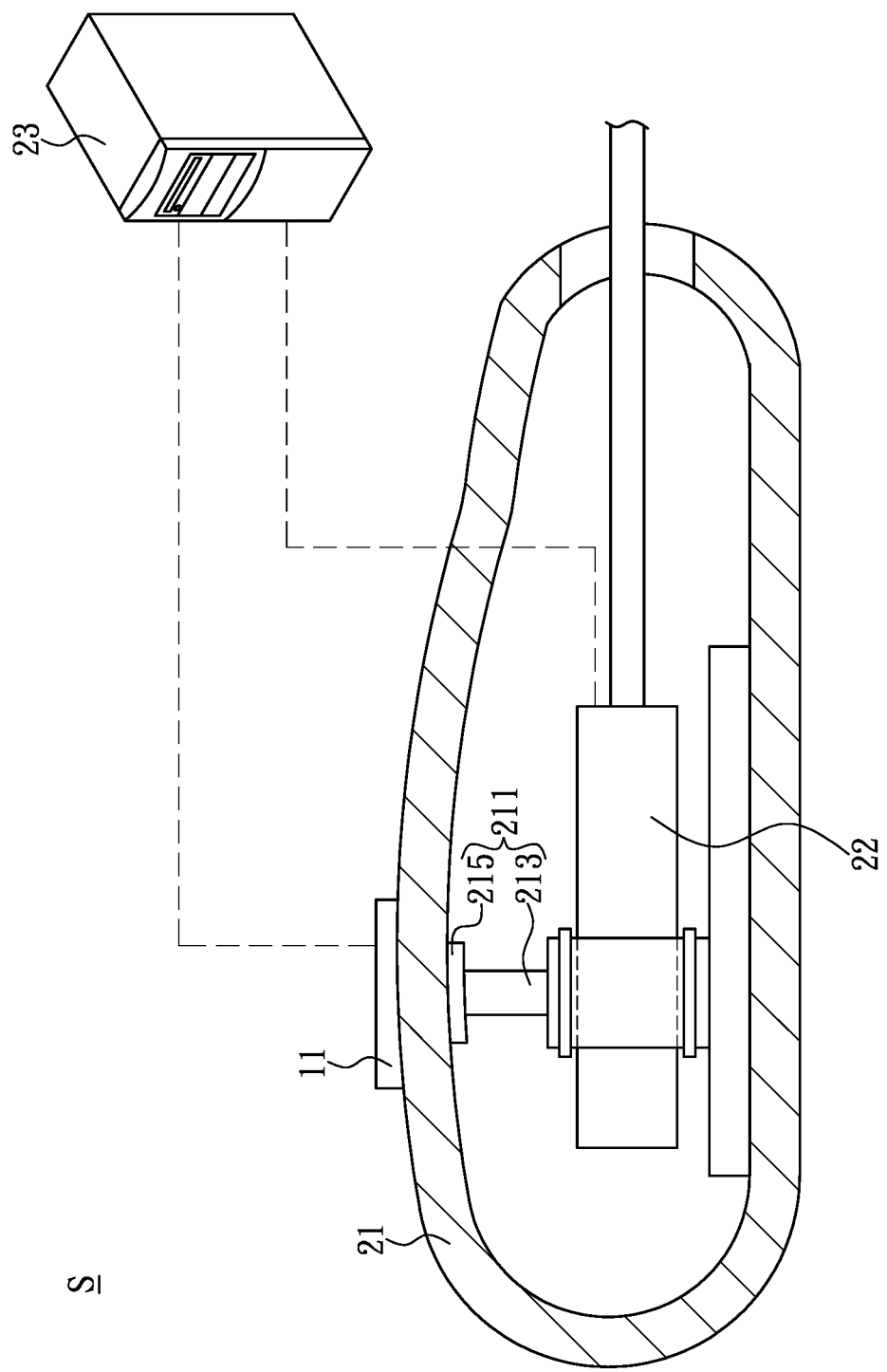
FIG. 5 is a schematic view of a system for establishing moving states recorded in a lookup table, showing also a sectional view of a dummy according to certain embodiments of the present disclosure.

The method for creating the contents of, or information in, the lookup table 110 is described below. Referring to FIG. 1, FIG. 2, and FIG. 5, the system S is used to establish the moving states recorded in the lookup table 110. The system S includes a dummy 21, a quantitative detector 22, an information processing device 23, the detection chip 11, and the radiation generation device 13. The dummy 21 has an elevating platform 211 for back-and-forth displacing at least a portion of the dummy 21 in order to simulate human body movements (e.g., the rise-and-fall breathing states of the human chest). In certain embodiments, the elevating platform 211 includes at least one linear driver 213 and a supporting table 215. The top side of the supporting table 215 abuts against the inner side of the dummy 21 while the bottom side of the supporting table 215 is connected to the linear driver 213. The linear driver 213 can move the supporting table 215 up and down automatically at a predetermined interval based on information preset by the user. It is noted that FIG. 5 serves only to illustrate the technical concept of the present disclosure. In practice, the elevating platform 211 may be so designed that a portion of the dummy 21 can be displaced three-dimensionally along three mutually perpendicular coordinate axes (e.g., forward/rearward, upward/downward, and leftward/rightward), and/or rotated along the three coordinate axes (e.g., cause that portion of the dummy 21 to pitch, yaw, and/or roll), so as to meet user needs.

With continued reference to FIG. 1, FIG. 2, and FIG. 5, the quantitative detector 22 can be extended into and received in the dummy 21. When the radiation emitters 133 of the radiation generation device 13 emit radiation toward different positions on the dummy 21 respectively, the quantitative detector 22 receives the radiation, and detects the data of the radiation received and the positions on the dummy 21 that correspond respectively to the different pieces of the radiation data detected. It is noted that FIG. 5 shows the quantitative detector 22 only schematically, and the present disclosure is not limited to a particular structure of the quantitative detector 22. As long as a quantitative detector can receive radiation and detect the data of the radiation received for subsequent use, it falls within the scope of the quantitative detector 22 of the present disclosure. The detection chip 11 can be fixed on the dummy 21, and the direction sensing module 113 can detect and acquire the moving state of the dummy 21, and generate a sensing message corresponding to the moving state. The first control module 112 can receive the sensing message, determine the movement information (e.g., an upward movement or downward movement) corresponding to the sensing message, and generate a movement message corresponding to the movement information.

As shown in FIG. 5, the information processing device 23 (e.g., a server or tablet computer) is electrically connected to the quantitative detector 22 and the detection chip 11 respectively so as to receive the movement message from the detection chip 11 and to receive from the quantitative detector 22 the radiation data and the information of the positions on the dummy 21 that correspond to the radiation data. The information processing device 23 may be configured to directly receive the data transmitted from the quantitative detector 22 and the detection chip 11, or receive the data indirectly should the data of the quantitative detector 22 and the detection chip 11 be stored in another device before this device relays the data to the information processing device 23. Both data transmission configurations fall within the scope of the electrical connection between the information processing device 23 and the quantitative detector 22 and the detection chip 11 that is defined in the present disclosure.

Figure 3:
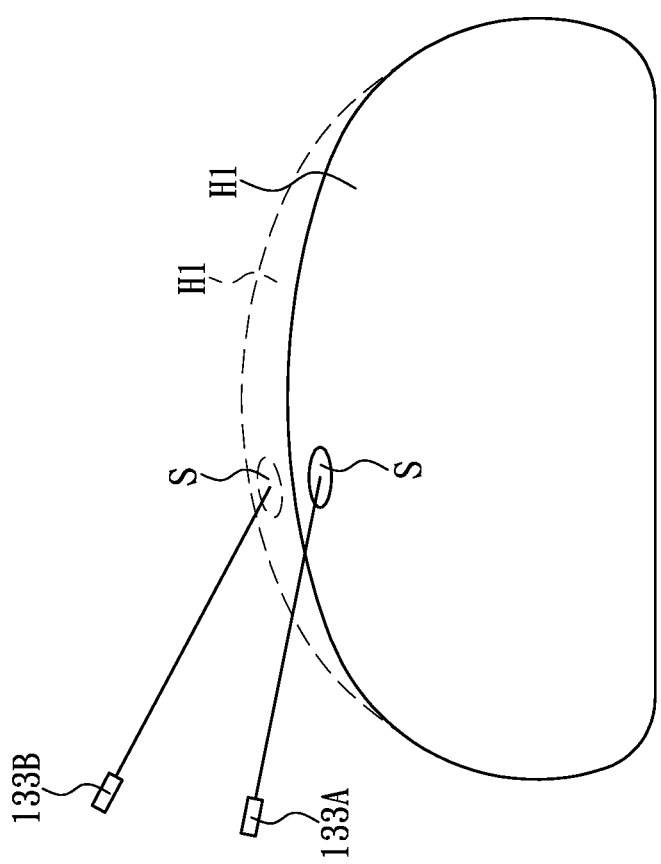
FIG. 3 is a schematic view showing a change in position of a tumor in a patient's chest while the patient exhales or inhales.

Referring to FIG. 3 for example, the positions on the dummy 21 that are subjected to the radiation of the radiation emitters 133A and 133B when the dummy 21 is simulating the exhaling state of the human chest H1 are different from those subjected to the radiation of the radiation emitters 133A and 133B when the dummy 21 is simulating the inhaling state of the human chest H1. Such information, for example, the positions on the dummy 21 that correspond to the radiation data, the radiation data, and/or the movement message, is received by the information processing device 23, and stored in a lookup table 110, 110' in the information processing device 23, such that the lookup table 110, 110' includes plural entries of movement information (e.g., exhaling state and inhaling state) and the radiation emitter number(s) (e.g., 133A and 133B) corresponding respectively to each entry of movement information. In certain embodiments, the stored plural entries of movement information may be converted, by the information processing device 23, from the movement messages received by the information processing device 23. The lookup table 110, 110' can be subsequently stored in the detection chip 11 or the radiation generation device 13. Therefore, the detection chip 11 or the radiation generation device 13 can generate control messages which includes information of, for example, the radiation emitter number(s) to be activated or deactivated, according to the contents of the lookup table 110, 110' and the detection result of the direction sensing module 113, and thereby activate or deactivate each of the radiation emitters 133 respectively so that each of the radiation emitters 133 emits or does not emit radiation.

Accordingly, when the system 1 and/or S is used in radiotherapy, the detection chip 11 can detect the current moving state of a patient's body and transmit a corresponding signal (i.e., the control message or the sensing message) to the radiation generation device 13 wirelessly. The patient, therefore, only has to have the detection chip 11 fixedly attached to the chest, and the detection chip 11 or the radiation generation device 13 will respectively activate or deactivate each of the radiation emitters 133 based on the current moving state (e.g., inhaling or exhaling) of the patient's body (e.g., the chest) and the contents of the lookup table 110, 110' so that each of the radiation emitters 133 emits or does not emit radiation. The system 1 and/or S does not require a large number of tubes or sensors to be provided around a patient's body, contrary to the conventional techniques such as respiratory gating, ABC, DIBH, and SIGRT. Moreover, the system 1 provides a non-invasive control means that not only helps enhance the comfortableness of a patient under radiotherapy, but also does not interfere with the propagation paths of radiation, thus featuring greater convenience of use than its conventional counterparts.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A system for adjusting radiation target sites according to moving states of a target object, comprising:
   a detection chip configured to be fixed on the target object and to detect and acquire a current moving state of the target object;
   a radiation generation device having a plurality of radiation emitters arranged to correspond to different positions on the target object respectively and configured to emit radiation when activated, and configured to transmit signals to and receive signals from the detection chip wirelessly; and
   a lookup table stored in the detection chip or the radiation generation device,
   wherein at least one of the detection chip and the radiation generation device is configured to respectively activate or deactivate each of the radiation emitters dynamically according to the current moving state of the target object and contents of the lookup table so that each of the respective radiation emitters emits or does not emit radiation.

2. The system according to claim 1, wherein the lookup table is stored in the detection chip, and the detection chip comprises:
   a direction sensing module configured to:
      detect and acquire the current moving state of the target object; and
      generate a sensing message corresponding to the current moving state.

3. The system according to claim 2, wherein the direction sensing module is configured to detect at least six degrees of freedom.

4. The system according to claim 3, wherein the detection chip is configured to detect rise-and-fall breathing states of a chest of a human body, and is configured to be mounted on the chest.

5. The system according to claim 4, wherein the lookup table comprises a plurality of entries of movement information and numbers of the radiation emitters that correspond respectively to the entries of the movement information; and the detection chip or the radiation generation device is configured to:
   identify one of the entries of the movement information that corresponds to the sensing message;
   record at least one number of at least one of the radiation emitters that corresponds to the corresponding entry of the movement information; and
   respectively activate or deactivate each of the radiation emitters according to the recorded number so that each of the respective radiation emitters emits or does not emit radiation.

6. The system according to claim 1, wherein the detection chip comprises:
   a direction sensing module configured to:
      detect and acquire the current moving state of the target object; and
      generate a sensing message corresponding to the current moving state;
   a wireless module configured to receive and send out the sensing message; and
   wherein the lookup table is stored in the radiation generation device.

7. The system according to claim 6, wherein the direction sensing module is configured to detect at least six degrees of freedom.

8. The system according to claim 7, wherein the detection chip is configured to detect rise-and-fall breathing states of a chest of a human body, and is configured to be mounted on the chest.

9. The system according to claim 8, wherein the lookup table comprises a plurality of entries of movement information and numbers of the radiation emitters that correspond respectively to the entries of the movement information; and the detection chip or the radiation generation device is configured to:
   identify one of the entries of the movement information that corresponds to the sensing message;
   record at least one number of at least one of the radiation emitters that corresponds to the corresponding entry of the movement information; and
   respectively activate or deactivate each of the radiation emitters according to the recorded number so that each of the respective radiation emitters emits or does not emit radiation.

10. The system according to claim 1, wherein the detection chip comprises a direction sensing module configured to detect at least six degrees of freedom.

11. The system according to claim 10, wherein the detection chip is configured to detect rise-and-fall breathing states of a chest of a human body, and is configured to be mounted on the chest.

12. The system according to claim 11, wherein the lookup table comprises a plurality of entries of movement information and numbers of the radiation emitters that correspond respectively to the entries of the movement information; and the detection chip or the radiation generation device is configured to:
   identify one of the entries of the movement information that corresponds to the sensing message;
   record at least one number of at least one of the radiation emitters that corresponds to the corresponding entry of the movement information; and
   respectively activate or deactivate each of the radiation emitters according to the recorded number so that each of the respective radiation emitters emits or does not emit radiation.

* * * * *